United States Patent [19]

Rockland et al.

[11] 4,088,140
[45] May 9, 1978

[54] DEMAND ANTI-ARRHYTHMIA PACEMAKER

[75] Inventors: Ronald H. Rockland, Wayzata; Thomas L. Jirak, Plymouth, both of Minn.

[73] Assignee: Medtronic, Inc., Minneapolis, Minn.

[21] Appl. No.: 697,470

[22] Filed: Jun. 18, 1976

[51] Int. Cl.² ............................................. A61N 1/36
[52] U.S. Cl. ........................ 128/419 PG; 128/419 D
[58] Field of Search ........ 128/419 P, 419 PG, 419 R, 128/421, 422, 423, 419 D

[56] References Cited

U.S. PATENT DOCUMENTS

| | | | |
|---|---|---|---|
| 3,144,019 | 8/1964 | Haber | 128/419 PG |
| 3,460,542 | 8/1969 | Gemmer | 128/419 PG |
| 3,557,796 | 1/1971 | Keller, Jr. et al. | 128/419 PG |
| 3,648,707 | 3/1974 | Greatbatch | 128/419 PG |
| 3,747,604 | 7/1973 | Berkovits | 128/419 PG |
| 3,857,398 | 12/1974 | Rubin | 128/419 D |
| 3,903,897 | 9/1975 | Woollons et al. | 128/419 PG |
| 3,937,226 | 2/1976 | Funke | 128/419 PG |
| 3,942,534 | 3/1976 | Allen et al. | 128/419 PG |
| 3,942,536 | 3/1976 | Mirowski et al. | 128/419 D |
| 3,949,759 | 4/1976 | Brownlee et al. | 128/419 PG |

*Primary Examiner*—William E. Kamm
*Attorney, Agent, or Firm*—Wayne A. Sivertson

[57] ABSTRACT

A demand anti-arrhythmia pacemaker having a plurality of electrodes adapted for connection to a heart for sensing depolarizations. A first responsive circuit provides stimulation signals to at least one area of the heart if a depolarization corresponding to a natural heartbeat fails to occur within a first predetermined time period. A second responsive circuit provides stimulation signals to the heart in a plurality of areas in response to sensed depolarizations which occur within a second predetermined time period.

27 Claims, 2 Drawing Figures

DEMAND ANTI-ARRHYTHMIA PACEMAKER

BACKGROUND OF THE INVENTION

The prevention of cardiac arrhythmias such as fibrillation has long been of interest in the art. Certain cardiac stimulation circuits have been developed to produce cardiac stimulation signals to prevent or stop fibrillation. One such device is disclosed in U.S. Pat. No. 3,937,226, issued to Dr. Herman D. Funke. In the Funke device, a plurality of electrodes are connected to a heart in spaced relation to each other for sensing depolarizations that occur at a plurality of areas of the heart. Output circuitry responsive to any sensed depolarization applies stimulation signals simultaneously to a plurality of areas of the heart rapidly after sensing a depolarization. The circuitry disclosed in the Funke patent includes a free running or astable multivibrator which generates a stimulation pulse to be applied to the plurality of areas of the heart if no depolarization signal is sensed within a predetermined time period. Thus, the Funke device acts to prevent premature ventricular contractions leading to ventricular fibrillation and has the capability to operate in a demand mode in the event of bradycardia or "skipped" beats, for example.

The circuitry of the Funke patent applies a stimulation signal to a plurality of areas on the heart each time the heart beats, even when the heart is beating at a normal rate. Consequently, a considerable amount of electrical power is used by the Funke device to stimulate the heart. Since the life of an implanted cardiac stimulation device is often dependent on the life of the power supply, it is considered highly desirable to reduce the drain on the power supply whenever possible.

SUMMARY OF THE INVENTION

The present invention comprises circuitry for sensing cardiac arrhythmias and applying appropriate stimulation signals to a heart which utilizes considerably less power than the prior art.

The reduction in power comsumption is achieved by applying cardioversion signals to a plurality of areas on the heart when depolarization signals are sensed within a time period corresponding to an unacceptably high beat rate, by pacing the heart at fewer areas when the natural heart rate falls below a predetermined minimum, and by not applying stimulation signals to the heart when the heart is beating naturally within a certain rate range. Thus, the apparatus of the present invention employs the multiple output stimulation system of Funke to cardiovert tachyarrhythmias and has the capability to operate in a demand mode in the event of bradycardia or "skipped" beats, at a considerable reduction in power requirements.

In a preferred embodiment, the present invention is formed of circuitry including a first path which applies a stimulation signal to one area of the heart if a depolarization corresponding to a naturally occurring heart beat fails to occur within a predetermined time period and a second path which applies a cardiac stimulation signal to a plurality of locations on the heart if depolarizations occur within a second predetermined time period. The first path is a demand pacing path which provides pacing signals in the event of "skipped" beats or bradycardia and the second path is a synchronous pacing path which provides cardioversion signals to stimulate a plurality of areas of the heart when a tachycardia exists. The present invention therefore operates as a demand pacer at a first rate, applies no stimulation to the heart up to a second higher rate, and above the second rate operates as a multiple electrode synchronous pacer for the prevention or correction of undesirable tachyarrhythmias.

DESCRIPTION OF THE PREFERRED EMBODIMENT

Figures 1, 2:
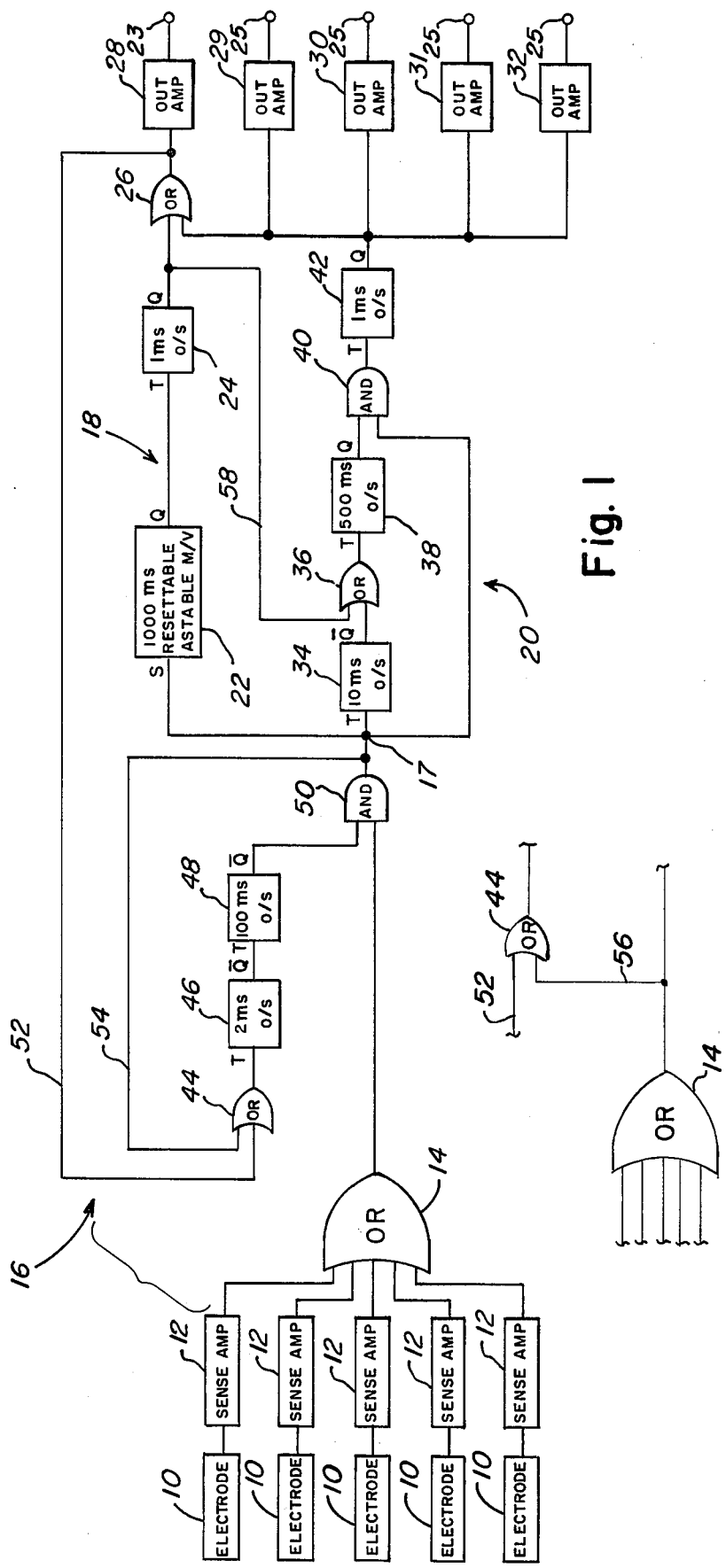
FIG. 1 shows a block diagram of a preferred embodiment of the present invention.
FIG. 2 shows a modification of the embodiment of FIG. 1.

Referring to FIG. 1, a circuit for demand pacing and cardioversion of tachyarrhythmias is shown. A plurality of electrodes 10 are adapted for connection in a spaced relation on a heart. Each electrode 10 is adapted for sensing depolarizations occurring in the area of the heart adjacent the electrode. Such electrodes for sensing cardiac depolarization signals are well known in the art and may be as described in the Funke patent referenced above, which is hereby incorporated by reference. Electrodes 10 are each connected to a sense amplifier 12 which may be any one of the amplifiers known in the art to be utilized with cardiac electrodes for amplifying sensed depolarizations. While five electrode-sense amplifier combinations are shown in the FIGURE, it is considered within the scope of the invention that a different number may be used for sensing depolarizations on a heart at a plurality of locations.

The output of each sense amplifier 12 is connected to one input of OR gate 14, which is a conventional gate for delivering at its output any signals applied to any one of its inputs in the order in which they are applied. The output of OR gate 14 is connected through a refractory determining circuit 16, which is described more fully below, to a junction 17. The junction 17 is common to a demand pacing circuit 18 and a synchronous anti-fibrillation circuit 20.

Demand pacing circuit 18 includes a resettable astable multivibrator or pulse generator 22 which is connected to junction 17 to be reset by sensed depolarization signals appearing at junction 17. Generator 22 has a timing period corresponding to a first heart beat rate, for example, a time period of 1,000 ms corresponding to a rate of 60 bpm. So long as generator 22 is reset by sensed depolarization signals at junction 17 which occur within 1,000 ms of one another, i.e., occurring at an effective rate of 60 or more bpm, the Q output of generator 22 is held low and not allowed to go high. The Q output of generator 22 is connected to pulse former 24 which may be a retriggerable one shot having a short duration pulse, such as 1 ms, triggered by a positive going pulse edge. The Q output of pulse former 24 is applied to an OR gate 26, the output of which is supplied to an output amplifier 28. Amplifier 28 may comprise any known form of output pulse amplifier suitable for use in cardiac pacemaker applications. The output of amplifier 28 is connected to a terminal 23 which is adapted for connection to an electrode, not shown, for applying stimulation signals to the heart at a single location.

Synchronous anti-fibrillation path or circuit 20 includes a delay circuit 34 connected to receive sensed depolarization signals appearing at terminal 17 at its input, or trigger terminal. The delay circuit 34 may be a retriggerable one shot having a short pulse duration of, for example, 10 ms. The output of delay circuit 34 is connected to one input of an OR gate 36, the output of which is connected to a retriggerable monostable multivibrator or one shot 38. The one shot 38 has a time period in its astable state corresponding to a second heart beat rate, as for example, a 500 ms time period corresponding to a rate of 120 bpm. The Q output of one shot 38 is connected to one input of AND gate 40 and the other input of AND gate 40 is connected directly back to junction 17. The output of AND gate 40 is connected to a short duration one shot pulse former 42, which may be identical to the pulse former 24 in the demand path 18. The output of pulse former 42 is connected to one input of OR gate 26 and is also connected directly to a plurality of output amplifiers 29 to 32. The output of each of the output amplifiers 28 to 32 is connected to a different terminal 25, the terminals 23 and 25 being adapted for connection for electrodes, now shown, positioned in spaced relation to each other for applying stimulation signals to the heart at a plurality of locations. Alternatively, terminals 23 and 25 may each be connected to a different one of the electrodes 10 which would then perform the function of both sensing depolarization signals and applying stimulation signals, in a known manner.

Because there is a finite conduction velocity even in the normal heart the plurality of sense electrodes 10, placed in a spaced relation on the heart, will sense depolarizations occurring during a single heart beat at slightly differing times. For example, normal conduction velocity in a normal heart is known to be approximately 80 ms. Therefore, the time between sensing the first depolarization and last depolarization relating to a single heart beat may be as much as 80 ms. A refractory circuit is necessary in order to aid the apparatus of the figure to differentiate between depolarizations that occur during a single heart beat and depolarization that may occur as the result of a tachycardia. A refractory circuit 16 is therefore connected between OR gate 14 and terminal 17.

Refractory circuit 16 includes an OR gate 44 having two inputs one input being connected by way of line 52 to the output of OR gate 26. The second input is connected by way of line 54 to junction 17. The output of OR gate 44 is connected to the input trigger of delay circuit 46 which may comprise a retriggerable one shot having a short duration time period of approximately 2 ms. The Q NOT output of delay circuit 46 is connected to the trigger input of refractory timer 48 which may comprise a retriggerable one shot having an astable state with a time period corresponding to the desired refractory period of, for example, 100 ms. Refractory periods of other durations may be considered more appropriate for other applications. The Q-NOT output of timer 48, which is normally high, is connected to one input AND gate 50. AND gate 50 is connected between the output of OR gate 14 and terminal 17 for gating the sensed depolarization signals to circuits 18 and 20. Other refractory circuit arrangements could be used. For example, a plurality of refractory circuits similar to circuit 16 could be inserted between sense amplifiers 12 and the inputs of OR gate 14, or sense amplifiers 12 could be constructed with a built-in refractory circuit.

The operation of the preferred embodiment is as follows. Electrodes 10 are connected in spaced relation on a heart for detecting depolarizations that occur in each area of the heart adjacent each electrode. In one example, one electrode is connected to the intraventricular septum and the other electrodes are connected in spaced relation on the heart ventricles. Depolarizations occurring adjacent an electrode 10 are sensed and amplified by sense amplifiers 12 and applied through OR gate 14 to one input terminal of AND gate 50. Refractory timer 48 is normally high, at its Q-NOT output, so that AND gate 50 is enabled to allow a pulse occurring at the output of OR gate 14 to be applied to terminal 17.

When the first sensed depolarization pulse is applied to terminal 17, at the output of AND gate 50, the pulse is also applied through OR gate 44 to delay circuit 46 which delays for a period of 2 ms before triggering refractory timer 48. The delay is necessary to assure that the depolarization pulse gets through before the refractory period is initiated. When refractory timer 48 is triggered, its Q-NOT output goes low, thereby causing AND gate 50 to be blocked for a period determined by the timer 48. This is the refractory period. Any sensed depolarizations amplified by amplifiers 12 and applied to AND gate 50 by OR gate 14 will be blocked from application to terminal 17 during the refractory period.

The sensed depolarization that does appear at terminal 17 is applied to set resettable astable multivibrator 22. So long as sensed depolarizations are applied to terminal 17, and thereby to the set input of multivibrator 22, within 1,000 ms of one another, astable multivibrator 22 will be continuously reset and no output pulse will occur. If, however, no depolarization pulse appears within 1,000 ms the Q output of multivibrator 22 will go high at the end of the 1,000 ms time period. This will cause pulse shaper 24 to be triggered and generate a 1 ms pulse at its Q output to be applied through OR gate 26 and output amplifier 28 to terminal 23 and thereby to an electrode connected to the heart. Circuit 18 therefore senses the failure of the heart to be beat within a first predetermined time period, and applies a stimulation pulse to the heart through output amplifier 28 to stimulate the heart to beat. Circuit 18 therefore operates as a demand pacer for pacing the heart in the event of a "skipped" beat or bradycardia.

The first pulse applied at terminal 17 also triggers the delay circuit 34, the Q-NOT output of which goes low for the duration of its astable state. At the end of the 10 ms delay period when the Q-NOT output goes high, this positive going edge is applied through OR gate 36 to the trigger input of one shot 38. The output of one shot 38 then goes high and is applied to one input of AND gate 40. Because the duration of a sensed depolarization pulse is less than 10 ms, the first depolarization pulse which triggers delay circuit 34 does not pass through AND gate 40. However, should a second depolarization pulse be applied to terminal 17 during the 500 ms period that the Q output of one shot 38 is high, the second depolarization pulse will pass through AND gate 40 and be appled to the trigger input of pulse shaper 42. A second depolarization pulse will also restart the 500 ms time period of one shot 38. When pulse shaper 42 is triggered, a pulse is applied at its Q output and through OR gate 26 and output amplifier 28 to terminal 23 and simultaneously to output amplifiers 29 to 32 and terminals 25. A stimulation pulse is thereby applied to a plurality of areas on a heart by a plurality of electrodes connected to terminals 23 and 25, in response to a sensed tachyarrhythmia. Circuit 20 operates as a synchronous multiple electrode pacer.

Whether an output stimulation pulse is produced by pulse shaper 24 or pulse shaper 42, it is applied through OR gate 26 and output amplifier 28 to terminal 23 which, along with its associated electrode, is common to both the demand pacing circuit 18 and the synchronous anti-fibrillation circuit 20. In either event, the pulse signal occurring at the output of OR gate 26 is applied through OR gate 44 to delay circuit 46 and, 2 ms later, to refractory timer 48. A refractory period is thereby initiated after each stimulation signal.

When a stimulation signal has been applied to the heart, it is desirable that demand circuit 18 and synchronous circuit 20 be conditioned to deal with arrhythmias that may later occur. Astable multivibrator 22 is reset by automatically returning to its reset position after applying a high going pulse edge to pulse shaper 24. It is also reset by a pulse which appears at junction 17. Likewise, because delay circuit 34 and one shot 38 are retriggerable they are reset and the 500 ms time period is restarted when a pulse is applied to junction 17. The possibility exists, however, that a tachycardia may occur after a stimulation pulse is generated by generator 22 in response to a bradycardia. Because the refractory period is immediately initiated by such a generated pulse the heart beat that occurs at that point and the associated depolarization signals will be blocked from application to synchronus circuit 20 by refractory circuit 16. Line 58 is therefore necessary as a connection between the output of pulse shaper 24 and OR gate 36 to immediately trigger one shot 38 to start its timing period when a pulse is generated by generator 22. Line 58 may be unnecessary when other refractory circuitry is used.

In the embodiment shown, with refractory connection line 54 connected between the output of AND gate 50 and an input to OR gate 44, a refractory period is immediately initiated upon the generation of a pulse appearing at the output of AND gate 50. This refractory period has a duration in the example given of 100 ms. In the patient with normal heart conduction velocity, all depolarizations associated with the same heart beat will have occurred before the end of the refractory period. However, in patients with slow conduction, such as those with a myocardial infarction, some depolarizations associated with the heart beat may not occur until after the end of the refractory period, thereby giving a false indication to the circuitry that a tachycardia is taking place. In those patients, it may be preferable to replace the connection 54 with a connection 56 to the output of OR gate 14 (See FIG. 2). With the input of OR gate 44 connected to the output of OR gate 14 by way of connection 56 those depolarizations which occur during the refractory period will retrigger refractory timer 48 so as to extend the refractory period for a time necessary to prevent false indications of a tachycardia from being applied to terminal 17. In the alternative, the refractory period as determined by timer 48 could be extended for a larger time by designing the timer to have a period of 160 ms, for example. However, in some patients with slow conduction, it may be difficult to predict the interval over which the heart will complete a single beat. In those cases, connection 56 would be preferable.

For a clearer understanding of what is considered to be the scope of this invention reference is made to the appended claims.

What is claimed is:

1. Cardiac electrical stimulation apparatus comprising: means for sensing depolarizations at at least two areas on a heart; first means having output means and responsive to the sensing means for providing cardiac stimulation signals to a plurality of areas on the heart in response to depolarizations occurring above a first predetermined rate; second means having output means responsive to the sensing means for providing cardiac stimulation signals to less than said plurality of areas on the heart in response to depolarizations occurring below a second predetermined rate.

2. Apparatus according to claim 1 wherein the sensing means comprise refractory means having a predetermined refractory period for responding either to sensed depolarizations or to stimulation signals to initiate the refractory period.

3. Apparatus according to claim 2 wherein the refractory means comprises: timing means for determining the predetermined refractory period; first means for initiating the timing means in response to said sensing means; second means for initiating the timing means in response to said first and second means; and means connecting said sensing means to said first and second means for inhibiting the response of the first and second means to the sensing means during the refractory period determined by the refractory timing means.

4. Apparatus according to claim 3 wherein the inhibiting means comprises gate means having an output, the first initiating means being connected to the output of the gate means and the second initiating means being connected to said first and second means output means.

5. Apparatus according to claim 3 wherein the inhibiting means comprises gate means having an input, the first initiating means connecting said sensing means to the input of the gate means and the second initiating means connecting said first and second means output means to the input of the gate means.

6. Cardiac electrical stimulation apparatus comprising: a plurality of electrode means adapted for connection in spaced relation on a heart; first means for responding to depolarization signals from the plurality of electrode means occurring below a first predetermined rate to provide stimulation signals to less than all of the plurality of electrode means; and second means for responding to depolarization signals from the plurality of electrode means occurring above a second predetermined rate to provide stimulation signals substantially to all of the plurality of electrode means.

7. Apparatus according to claim 6 wherein the first means comprises multivibrator means resettable by said depolarization signals for providing a stimulation signal at the end of a first time period corresponding to said first rate to at least one of the plurality of electrode means.

8. Apparatus according to claim 9 wherein the first means comprises multivibrator means resettable by said depolarization signals for providing a stimulation signal at the end of a first time period corresponding to said first rate to at least one of the plurality of electrode means.

9. Apparatus according to claim 6 wherein the second means comprise: multivibrator means responsive to a first depolarization signal for changing state for a second time period corresponding to the second rate; and gate means responsive to the multivibrator means for initiating a stimulation signal at all of the plurality of stimulation electrode means in response to a second depolarization signal occurring during the second time period.

10. Cardiac electrical stimulation apparatus comprising: a plurality of sensing electrode means adapted to be connected in space relation on a heart; at least two stimulation output means adapted to be connected in spaced relation on a heart; first means for responding to depolarization signals from the plurality of sensing electrode means occurring below a first predetermined rate to provide stimulation signals to at least one of the stimulation electrode means; and second means for responding to depolarization signals from the plurality of sensing electrode means occurring above a second predetermined rate to provide stimulation signals to a plurality of stimulation output means.

11. Apparatus according to claim 10 wherein the first means comprises multivibrator means resettable by said depolarization signals for providing a stimulation signal at the end of a first time period corresponding to said first rate to said one stimulation output means.

12. Apparatus according to claim 10 wherein the second means comprise: multivibrator means responsive to a first depolarization signal for changing state for a second time period corresponding to the second rate; gate means responsive to the multivibrator means for initiating a stimulation signal at said plurality of stimulation output means in response to a second depolarization signal occurring during the second time period.

13. Apparatus according to claim 12 wherein the first means comprise multivibrator means resettable by said depolarization signals for providing a stimulation signal at the end of a first time period corresponding to said first rate to said one stimulation output means.

14. Apparatus according to claim 10 wherein said plurality of stimulation output means includes said one stimulation output means.

15. Apparatus according to claim 10 whereis each of said stimulation output means are adapted for connection to a different one of said sensing electrode means.

16. Cardiac electrical stimulation apparatus comprising: means for sensing depolarization at a plurality of areas on a heart; first means for providing a cardiac stimulation signal in the absence of sensed depolarizations during a first time period; and second means for providing a cardiac stimulation signal upon the occurrence of sensed depolarization within a second time period shorter than said first time period.

17. Apparatus according to claim 16 wherein the first means further comprises retriggerable multivibrator means responsive to the absence of a sensed depolarization for changing state at the end of the first time period to produce a cardiac stimulation pulse.

18. Apparatus according to claim 17 wherein the first means comprises means for providing a cardiac stimulation signal at a single area on the heart.

19. Apparatus according to claim 16 wherein the second means further comprises: multivibrator means connected for responding to a first sensed depolarization for changing state for the second time period; and gate means responsive to the multivibrator means for initiating a cardiac stimulation signal upon the occurrence of a second sensed depolarization during the second time period.

20. Apparatus according to claim 19 wherein the first means further comprise retriggerable multivibrator means connected for responding to the absence of a sensed depolarization for changing state at the end of the first time period to produce a cardiac stimulation pulse.

21. Apparatus according to claim 20 wherein the demand means comprise means for providing a cardiac stimulation signal at a single area of the heart.

22. Apparatus according to claim 21 wherein the second means comprises means for providing a cardiac stimulation signal at a plurality of areas on the heart simultaneously.

23. Cardiac electrical stimulation apparatus comprising: means for sensing depolarization at a plurality of areas on a heart; first means connected to the sensing means for applying a stimulation signal to a heart at at least a single area on the occurrence of a bradycardia, and second means connected to the sensing means for applying a stimulation signal to a plurality of areas on a heart on the occurrence of a tachycardia.

24. Apparatus according to claim 23 wherein the first means comprises multivibrator means for generating a stimulation signal upon the failure to sense a depolarization within a first predetermined time period.

25. Apparatus according to claim 23 wherein the second means comprise means for generating a stimulation signal upon the occurrence of a second sensed depolarization within a second predetermined time period after the occurrence of a first sensed depolarization.

26. Apparatus according to claim 23 wherein the sensing means comprise refractory means for blocking sensed depolarizations from the first and second means for a predetermined refractory period after the occurrence of either a sensed depolarization or a stimulation signal.

27. Implantable cardiac electrical stimulation apparatus comprising: means for sensing cardiac depolarization; means for providing a cardiac pacing signal in the absence of sensed depolarizations during a first time period; and means for providing a cardioverting signal to a plurality of areas of the heart upon the occurrence of sensed depolarization within a second time period shorter than said first time period.

* * * * *